United States Patent
Tang et al.

(10) Patent No.: US 11,510,566 B2
(45) Date of Patent: Nov. 29, 2022

(54) SYSTEMS AND METHODS FOR VISION TESTING

(71) Applicant: Essilor International, Charenton-le-Pont (FR)

(72) Inventors: David Tang, Charenton-le-Pont (FR); Bruno Moinard, Charenton-le-Pont (FR); Damien Rousseau, Charenton-le-Pont (FR); Andrea Molinaro, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 485 days.

(21) Appl. No.: 16/332,479

(22) PCT Filed: Mar. 24, 2017

(86) PCT No.: PCT/EP2017/057132
§ 371 (c)(1),
(2) Date: Mar. 12, 2019

(87) PCT Pub. No.: WO2018/050297
PCT Pub. Date: Mar. 22, 2018

(65) Prior Publication Data
US 2021/0290051 A1 Sep. 23, 2021

Related U.S. Application Data

(60) Provisional application No. 62/394,515, filed on Sep. 14, 2016.

(51) Int. Cl.
*A61B 3/032* (2006.01)
*A61B 3/00* (2006.01)
(Continued)

(52) U.S. Cl.
CPC .............. *A61B 3/032* (2013.01); *A61B 3/005* (2013.01); *A61B 3/0033* (2013.01); *A61B 3/0285* (2013.01); *G06F 3/04883* (2013.01)

(58) Field of Classification Search
CPC .. A61B 3/08; A61B 3/09; A61B 3/032; G02F 3/04886
(Continued)

(56) References Cited

U.S. PATENT DOCUMENTS 2,371,999 A * 3/1945 Isaacson .................. A61B 3/08
351/201
7,597,445 B2 * 10/2009 Sakurada ................. A61B 3/08
351/243
(Continued)

FOREIGN PATENT DOCUMENTS

| CN | 102458220 A | 5/2012 |
|---|---|---|
| CN | 102573610 A | 7/2012 |

(Continued)

OTHER PUBLICATIONS

International Search Report dated Jun. 29, 2017 in PCT/EP2017/057132 filed on Mar. 24, 2017.
(Continued)

*Primary Examiner* — Zachary W Wilkes
(74) *Attorney, Agent, or Firm* — Oblon, McClelland, Maier & Neustadt, L.L.P.

(57) ABSTRACT

A vision testing device includes a light-occluding casing for administering vision tests. A viewing station is coupled to the light-occluding casing so a test subject can see a first digital display housed within the light-occluding casing. A second digital display is external to the light-occluding casing and is configured to receive touch-based input. One or more predetermined vision tests are displayed via the first digital display. The second digital display receives input
(Continued)

corresponding to the vision test displayed via the first digital display. The second digital display includes response indicators that can be activated via a swiping motion on the second digital display, and a response is recorded as a result of the swiping motion. Each answer corresponding to a swiping motion is stored and output as a result of the vision test.

12 Claims, 12 Drawing Sheets

(51) Int. Cl.
*A61B 3/028* (2006.01)
*G06F 3/04883* (2022.01)
(58) Field of Classification Search
USPC .................................. 351/222, 223, 201, 202
See application file for complete search history.

(56) References Cited

U.S. PATENT DOCUMENTS

| | | | | |
|---|---|---|---|---|
| 7,690,790 B2* | 4/2010 | Hosoi | ..................... | A61B 3/032 |
| | | | | 351/242 |
| 7,819,524 B2* | 10/2010 | Kanazawa | ........... | H04N 13/327 |
| | | | | 351/201 |
| 8,087,781 B2* | 1/2012 | Kanazawa | ................ | A61B 3/08 |
| | | | | 351/240 |
| 8,888,288 B2* | 11/2014 | Iravani | .................... | A61B 3/063 |
| | | | | 351/223 |
| 9,055,904 B2* | 6/2015 | Yoo | ....................... | A61B 3/0041 |
| 9,298,367 B1 | 3/2016 | McDaniel et al. | | |
| 9,492,075 B2* | 11/2016 | Schroth | .................. | A61B 3/085 |
| 9,572,486 B2* | 2/2017 | Voigtmann | ............... | A61B 3/08 |
| 10,194,795 B2* | 2/2019 | Nauche | ................ | A61B 3/0033 |
| 2010/0033678 A1 | 2/2010 | Foster | | |
| 2011/0025977 A1* | 2/2011 | Yoo | .......................... | A61H 5/00 |
| | | | | 351/203 |
| 2011/0027766 A1 | 2/2011 | Yoo et al. | | |
| 2012/0050685 A1 | 3/2012 | Bartlett et al. | | |
| 2012/0188507 A1 | 7/2012 | Foster | | |
| 2014/0218682 A1 | 8/2014 | Foster | | |
| 2015/0015493 A1 | 1/2015 | Hsieh | | |
| 2015/0335235 A1 | 11/2015 | Pisani | | |
| 2017/0000328 A1* | 1/2017 | Nauche | ................. | A61B 3/032 |

FOREIGN PATENT DOCUMENTS

| | | |
|---|---|---|
| CN | 103246382 A | 8/2013 |
| CN | 104994776 A | 10/2015 |
| CN | 105848563 A | 8/2016 |
| FR | 3 014 673 A1 | 6/2015 |
| JP | 2014-140482 A | 8/2014 |
| WO | WO 2016/116933 A1 | 7/2016 |

OTHER PUBLICATIONS

Combined Chinese Office Action and Search Report dated Mar. 9, 2021 in Chinese Patent Application No. 201780056103.1 (with English translation), 20 pages.
European Office Action dated Mar. 21, 2022 in European Patent Application No. 17 713 639.7 filed Mar. 24, 2017, 8 pages.

* cited by examiner

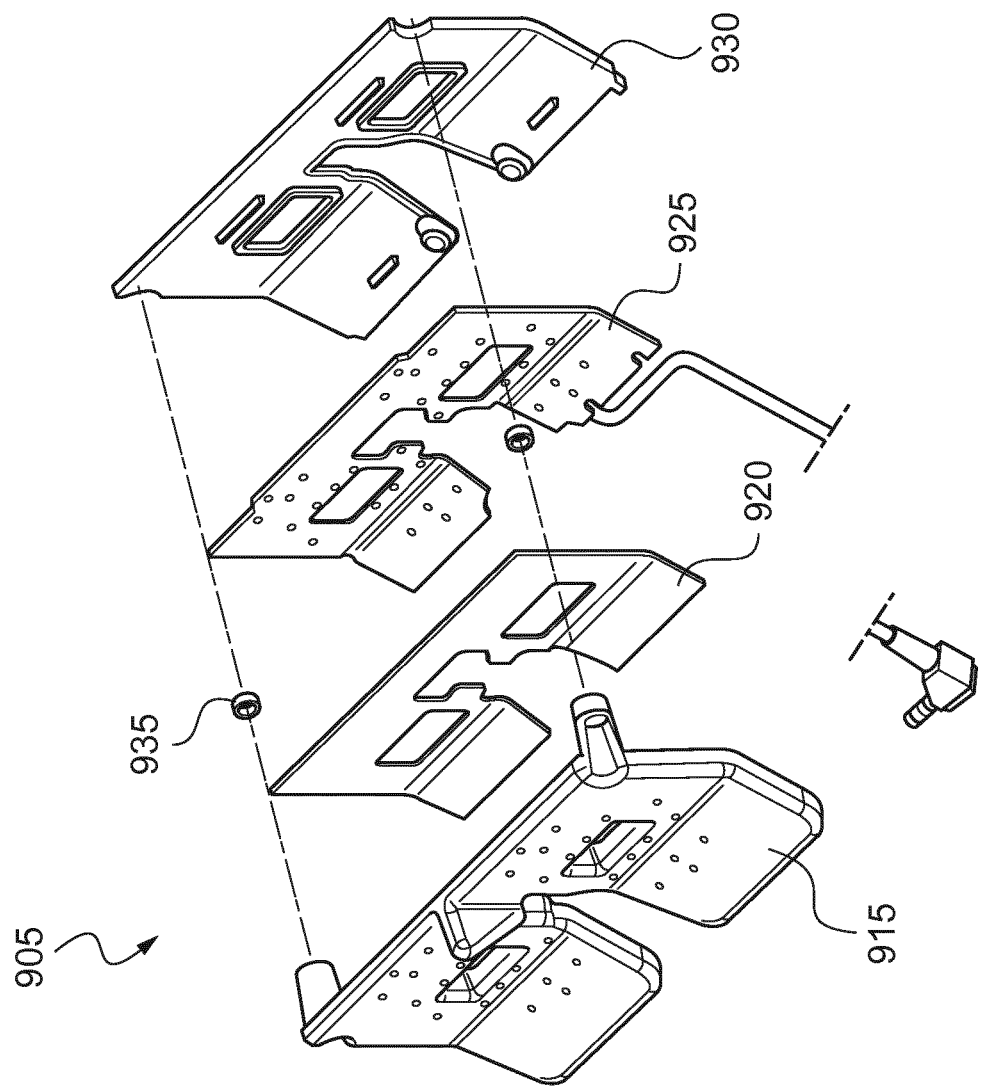

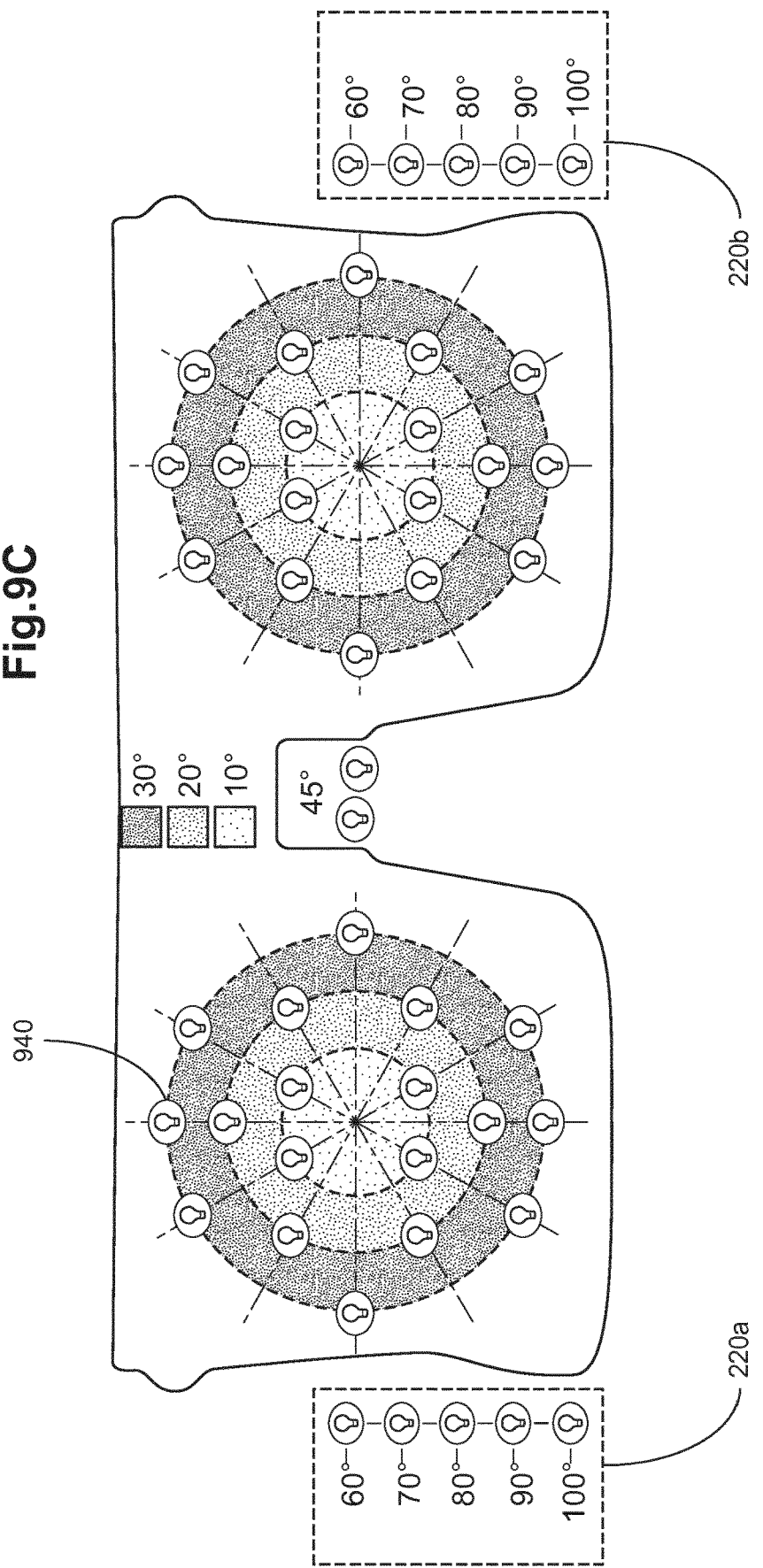

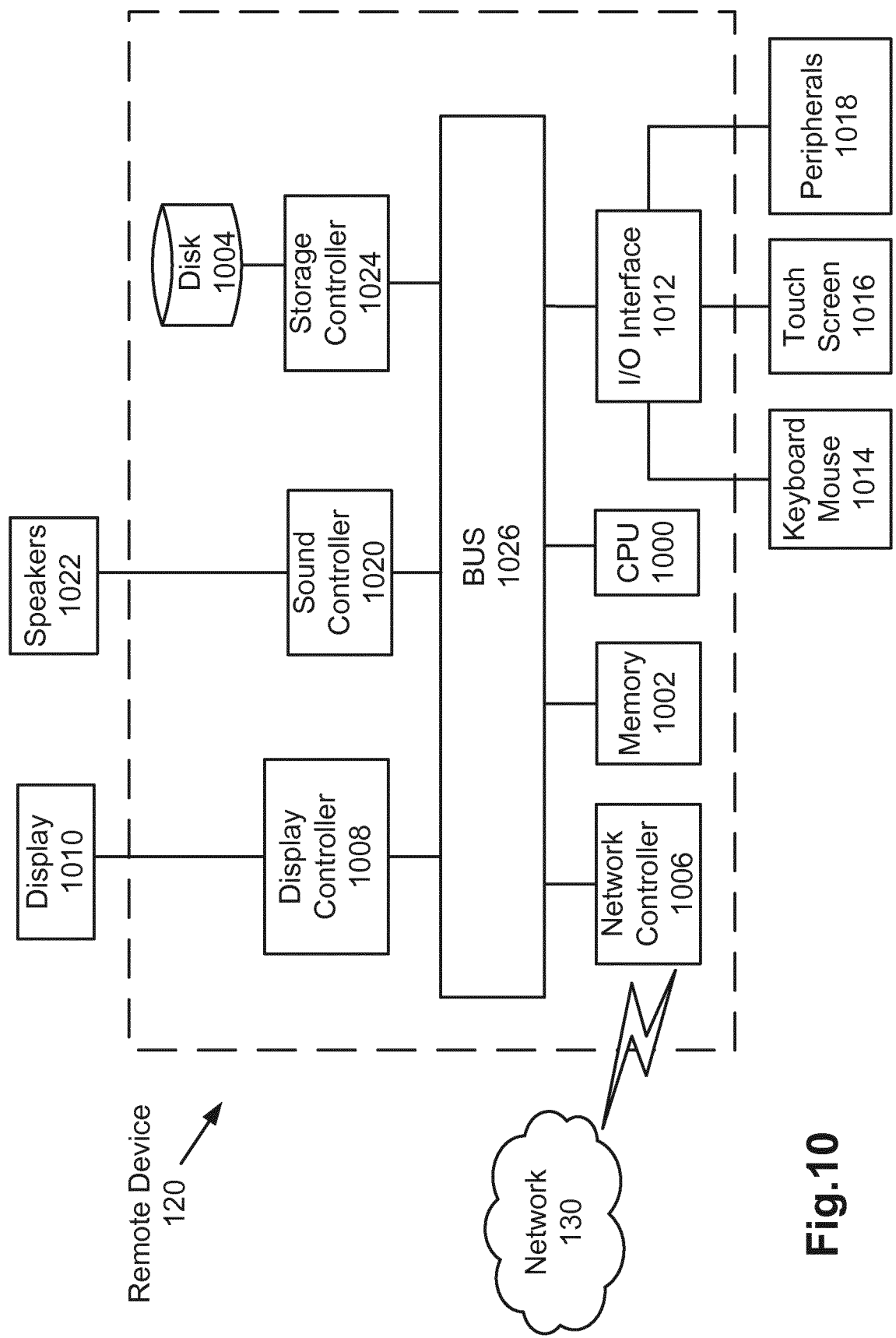

SYSTEMS AND METHODS FOR VISION TESTING

CROSS-REFERENCE TO RELATED APPLICATION

The present application claims the benefit of U.S. Provisional Application No. 62/394,515, filed Sep. 14, 2016, the entire contents of which being incorporated herein by reference.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Vision testing devices can be used for visual screening in a variety of applications, including use by eye care professionals, departments of motor vehicles, schools, and the military. Typical vision screening can be slow, limited, and subjective. Vision testing devices have been developed in an attempt to improve speed, but they continue to fall short in many aspects. For example, vision screening using a vision testing device is typically administered by an operator for a test subject. The test subject looks at or into the device, and the operator controls the device, elicits a series of responses to questions from the test subject about what they see in or on the device, and records the test subject responses. Such procedures can result in errors based on human factors or subjective answers and records.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

According to embodiments of the disclosed subject matter, a vision testing device can include a light-occluding casing for administering vision tests. A viewing station can be coupled to the light-occluding casing so a test subject can see a first digital display housed within the light-occluding casing. A second digital display can be external to the light-occluding casing and can be configured to receive touch-based input. One or more predetermined vision tests can be displayed via the first digital display. The second digital display can receive input corresponding to the vision test displayed via the first digital display. The second digital display can include response indicators that can be activated via a swiping motion on the second digital display, and a response can be recorded as a result of the swiping motion. Each answer corresponding to a swiping motion can be stored and output as a result of the vision test. This summary does not list all necessary characteristics, and therefore, sub-combinations of these characteristics may also constitute an embodiment.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 9B is an exploded view of a mask insert for the vision testing device according to one or more exemplary aspects of the disclosed subject matter;

FIG. 9C depicts light positions in a mask insert according to one or more aspects of the disclosed subject matter; and FIG. 10 is a hardware block diagram of a remote device according to one or more exemplary aspects of the disclosed subject matter.

DETAILED DESCRIPTION

Figure 1:
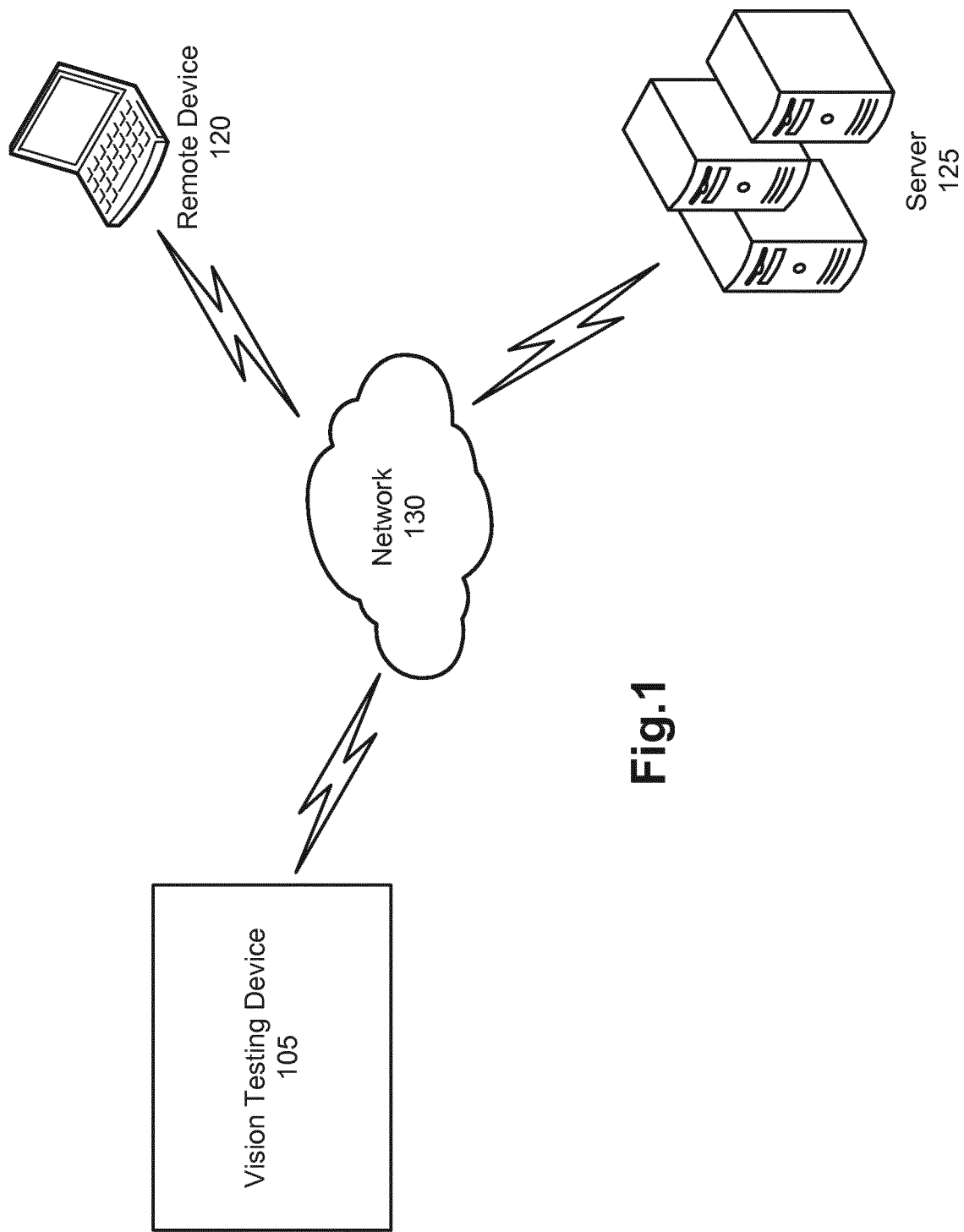
FIG. 1 depicts an exemplary overview of a vision testing system according to one or more aspects of the disclosed subject matter.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one embodiment" or "an embodiment" means that a particular feature, structure, characteristic, operation, or function described in connection with an embodiment is included in at least one embodiment of the disclosed subject matter. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments. Further, it is intended that embodiments of the disclosed subject matter can and do cover modifications and variations of the described embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the disclosed subject matter to any particular orientation or configuration. Further more, terms such as "first," "second," "third," etc., merely identify one of a number of portions, components, points of reference, operations and/or functions as described herein, and likewise do not necessarily limit embodiments of the disclosed subject matter to any particular configuration or orientation.

Referring now to the drawings, wherein like reference numerals designate identical or corresponding parts throughout the several views.

FIG. 1 depicts an exemplary overview of a vision testing system 100, herein referred to as system 100, according to one or more aspects of the disclosed subject matter. The system 100 can include a vision testing device 105 connected to a remote device 120 and a server 125 via a network 130. The vision testing device 105 can represent one or more vision testing devices. The system 100 can administer one or more predetermined tests via the vision testing device 105. One or more predetermined tests can be administered on-demand and/or can be stored and administered as part of a protocol, as further described herein. Many vision tests are available. For example, vision tests can be in various categories including preliminary tests, refractive tests, non-refractive tests, horizontal peripheral tests, and the like. For example, preliminary tests can include loss of accommodation test, as well as visual acuity tests. Visual acuity tests can include letters, numbers, Landolts, Snellen, E-Tumbling, Early Treatment Diabetic Retinopathy Study, and the like. Refractive tests can include ametropia red/green, astigmatism, latent hyperopia, fusion, lateral and vertical phoria, depth perception, and the like. Non-refractive tests can include color tests, contrast sensitivity tests, and the like. Horizontal peripheral vision tests can include stimuli at 60°, 70°, 80°, 85°, 80°, 100° and 55° temporal, and 45° nasal. Vertical peripheral vision tests can also be administered using a mask insert as further described herein. Additional tests can include HOTV tests, road sign recognition tests, Allen tests, and the like. Additionally, testing conditions can be chosen for each test including night, day, glare, monocular left and right, binocular, distance, intermediate, near, and the like. The testing conditions can be changed at any time including while a test is being administered.

The remote device 120 can represent one or more remote devices connected to the vision testing system 105 and the server 125 via the network 130. The remote device 120 can be a computer, a laptop, a tablet, a smart phone, a PDA, and the like. The remote device 120 can include processing circuitry to independently operate and/or assist in operating the system 100. The remote device 120 can include an interface, such as a digital and/or physical keyboard and/or a mouse and/or touch-based input functionality, allowing an operator, for example, to interact with vision testing device 105. The remote device 120 can operate to select and iniate one or more predetermined tests, select and/or change the testing conditions, view answers of a user of the vision testing device 105, create protocols, create a patient profile, and the like.

The server 125 can represent one or more servers connected to the vision testing device 105 and the remote device 120 via the network 130. The server 125 can include processing circuitry to perform various processing for the system 100 including receiving requests from one or more of the vision testing device 105 and the remote device 120 via the network 130. Additionally, the server 125 can transmit information to one or more of the vision testing device 125 and the remote device 120 via the network 130.

The network 130 can represent one or more networks connecting the vision testing device 105, the remote device 120, and the server 125. The network 130 can be a public network, such as the Internet, or a private network such as an LAN or WAN network, or any combination thereof and can also include PSTN or ISDN sub-networks. The network 130 can also be wired, such as an Ethernet network or a USB port, or can be wireless such as a cellular network including EDGE, 3G 4G, and LTE/LTE-A wireless cellular systems. The wireless network can also be Wi-Fi, Bluetooth, or any other wireless form of communication that is known.

Figure 2:
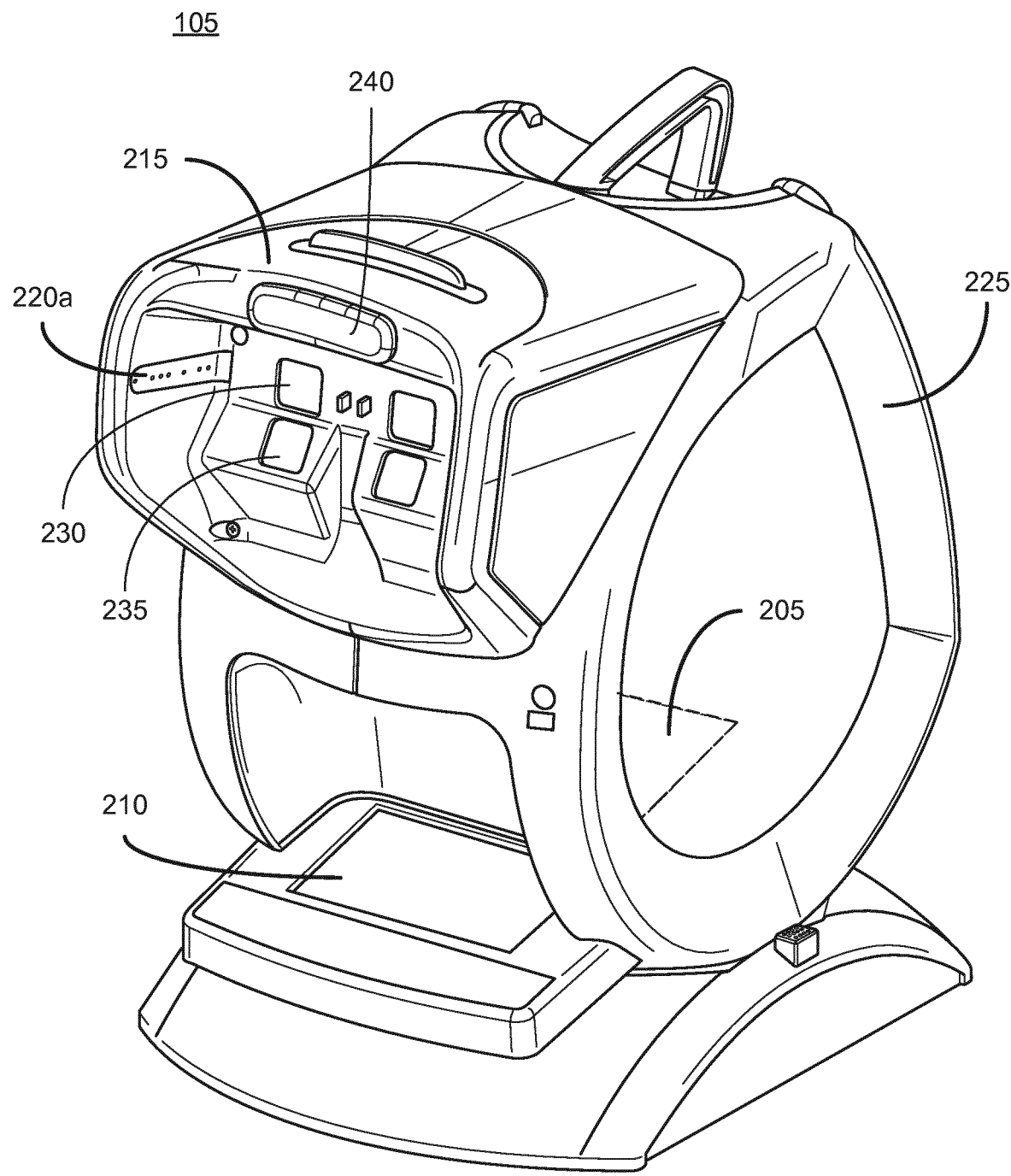
FIG. 2 depicts an exemplary perspective view of a vision testing device according to one or more aspects of the disclosed subject matter.
Figure 9A:
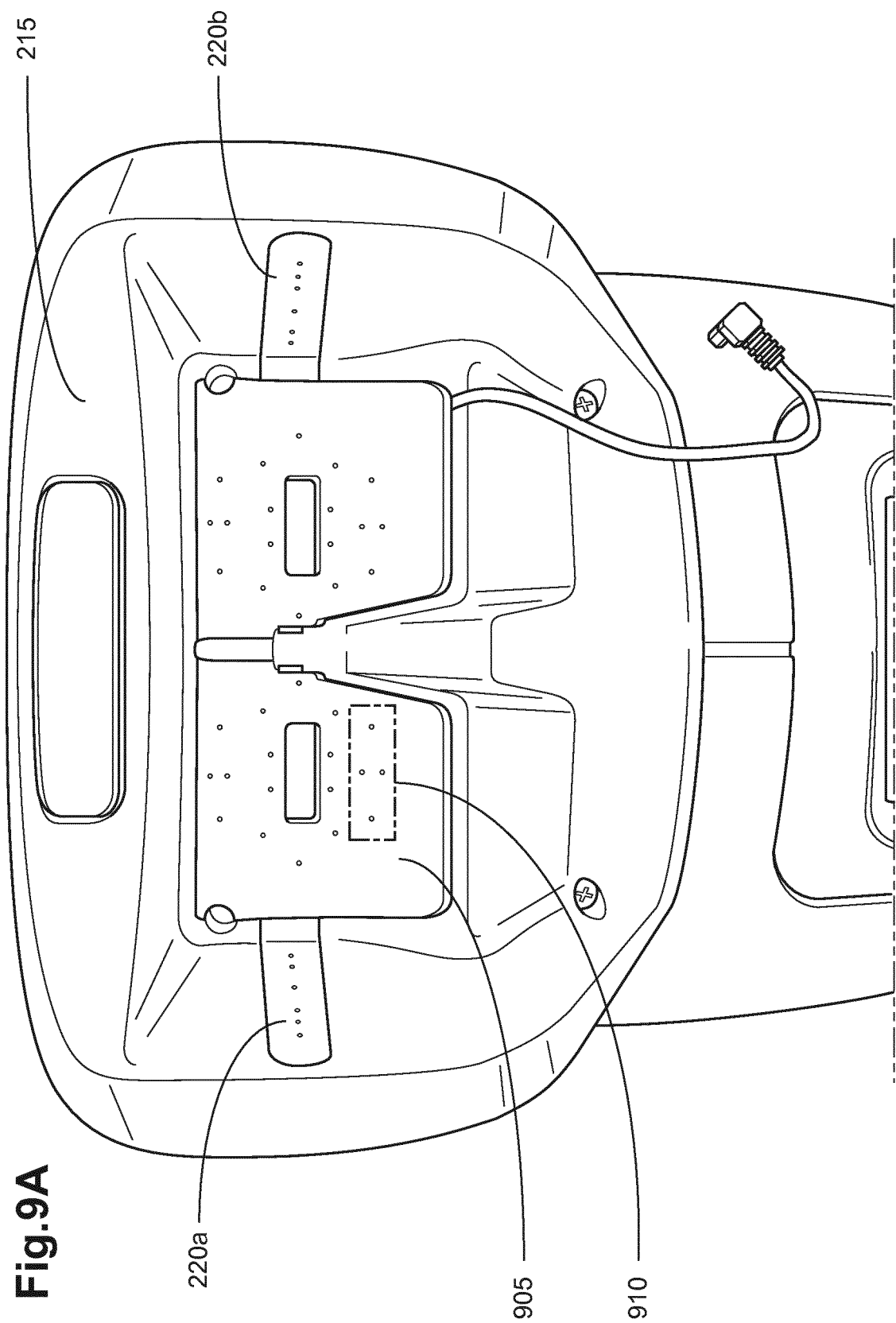
FIG. 9A is a perspective view of a mask insert for the vision testing device according to one or more exemplary aspects of the disclosed subject matter.

FIG. 2 depicts an exemplary perspective view of the vision testing device 105 according to one or more aspects of the disclosed subject matter. The vision testing device 105 can include a first portion of a digital display 205, a second portion of the digital display 210, a viewing station 215, and a first LED strip 220a of a mirrored LED strip pair. The first LED strip 220a can be part of a pair of LED strips 220a, 220b, as seen in FIG. 9A, wherein the first LED strip 220a extends from a left side of the viewing station 215 and the second LED strip 220b extends from a right side of the viewing station 215. The LED strip pair 220a, 220b can be positioned at about the same height as a top viewing portion of the viewing station 215. The LED strip pair 220a, 220b can be configured to assist in administering a horizontal and/or vertical peripheral vision test, for example. More specifically, each LED strip 220a, 220b can include a plurality of holes through which light from one or more LEDs is visible when the one or more LEDs are activated. The light from the one or more LEDs can be activated for one or more predetermined holes in one or more of the LED strips in a predetermined order corresponding to the horizontal and/or vertical peripheral vision test, for example. The viewing station 215 can be configured for a test subject to look into the vision testing device 105 and see display test patterns. Viewing station 215 can include a pair of eyepieces for far vision 230 and a pair of eyepieces for near vision 235. Viewing station 215 can also include a face rest 240, upon which a test subject can rest their forehead to place their head in a suitable position for performing the vision screening.

The first portion of the digital display 205 and the second portion of the digital display 210 can be portions of one digital display. The first portion of the digital display 205 can be housed within a light occluding casing 225 of the vision testing device 105. Additionally, the first portion of the digital display 205 can be configured to display one or more predetermined vision tests to be viewed through the viewing station 215. The viewing station 215 can be optically configured to view the first portion of the digital display 205 when a patient is using the vision testing device 105. The second portion of the digital display 210 can be positioned such that the second portion of the digital display 210 is in plain view, thereby being accessible to a user of the vision testing system 105 while the user is using the vision testing system 105. The second portion of the digital display 210 can be configured to receive touch-based input, wherein the touch-based input can correspond to answers for one or more predetermined vision tests as further described herein. It should be appreciated that each of the first portion of the digital display 205 and the second portion of the digital display 210 can be independent displays such that the first portion of the digital display 205 can be placed in various locations within the light-occluding casing of the vision testing device 105 without affecting the position of the second portion of the digital display 210. The first and/or second portion of the digital display can be a touch-based LCD display, for example. Alternatively, or additionally, the second portion of the digital display 210 can be a non-display input device including a joy stick, track pad, and the like, wherein the non-display input device can be communicably coupled to the first portion of the digital display 205, which can be a single, independent digital display, so that the user can respond to the one or more vision tests displayed via the first portion of the digital display 205 using the non-display input device.

The vision testing device 105 can include processing circuitry and memory to store a test library and cause the vision testing device 105 to administer one or more vision tests. The memory can be local memory and/or remotely accessible memory including a database, server 125, and the like, for example. Alternatively, or additionally, the remote device 120 can transmit instructions to administer the one or more vision tests. The vision testing device 105 provides a controlled testing environment, in that it controls the parameters of distance and light during the vision testing. The vision testing device 105 includes an optical path to ensure that the testing distance is always accurate and conformed to the standard for near, far and intermediate distances. The vision testing device 105 also includes lighting, such as one or more LEDs, and controls for the lighting, within the casing, making sure that the light is calibrated and constant.

The vision testing device 105 provides a new way to interact with the test subject, wherein the test subject can be a user, patient, and the like. Instead of the device audibly going through a series of questions and the test subject pushing a button in response to the correct answer, the test subject can swipe an external screen, wherein the external screen can include the second digital display 210, for example, in a direction indicating the correct response. For example, the first digital display 205 may display standard C-Landolt or E and the device may ask the test subject to swipe in the direction that the C or E opens. This system may reduce the likelihood of a test subject misunderstanding the vision testing device 105, as well as reduce the time needed to elicit a response from the test subject by providing multiple response choices at once instead of in series.

The vision testing device 105 may be pre-programmed by an operator to administer a desired test protocol, the protocol being a series of vision tests, including various conditions to fit the needs of the application including recreating real-world scenarios, for example.

The vision testing device 105 may include an auto-mode. The auto-mode may be fully embedded in the device and provide a controlled testing environment. The auto-mode may be non-operator dependent. The test subject can self-administer the test and record answers. As a result, the time needed to administer the vision test can be reduced, and the efficiency of the test subject flow within an eye care practice or other administration facility may be reduced. For example, the devices can be installed in the pre-screening room, or a dispensing area, saving valuable time for the doctor in the exam lane.

Additionally, the vision testing device 105 may remove subjectivity or bias of the operator, and thus allow for a more objective result. For example, in the military, pilots may receive vision tests to determine if they can fly. This scenario can add significant pressure to the operator as the results of the vision test may make or break the pilot's career. Therefore, the objectiveness of the vision testing device 105 can be advantageous for military testing.

The auto-mode may be non-audio dependent. Preliminary instructions may be given in three different ways: audio, text, and pictograms, and the device may administer a trial test. Therefore the test subject may be guided in how to perform the test, and there are multiple instruction formats that may be understood regardless of language, hearing, or reading capacities. For example, the test process may not start until the trial test is answered correctly, thus allowing confirmation of understanding and reducing the likelihood of errors by the test subject during testing. Once the tests starts, each vison test may be displayed automatically without further audio instructions.

The vision testing device can receive a "swipe" response, as further described herein. The "swipe" is unique in the context of vision screening on a vision testing device, and provides a robust response method that reduces test subject errors. For example, recording a response can be based on the direction and intensity/length of the "swipe". The vision testing device 105 may be configured to receive a touch based input in the form of a swipe, wherein the swipe movement is long enough to activate all response zones in a response indicator, as further described herein. Alternatively, the system could use a series of taps, pinches, swipes or any combination that together trigger all the response zones. These configurations can avoid errors that occur with a single tap or click because the response is not recorded until all of the progression bars are full, or in other words, when all response zones in a response indicator have been activated. If the test subject has second thoughts, the test subject can stop the movement before completing the response zones, and swipe in another direction.

The test protocols used in the auto-mode can be configured to be administered in a predetermined order based on the test subject's needs, for example. Additionally, once a test protocol is launched, it may progress automatically and record the test subject's answers without further input from the operator. For example, in the C-Landolt acuity test, each time the test subject answers correctly by swiping in the correct direction, the next C-Landolt may automatically be displayed with a smaller acuity. When answered incorrectly, the device may go back to the previous acuity level. If answered twice incorrectly for the same level, the device may stop the process for the C-Landolt acuity test and move to the next visual acuity test.

Figure 3:
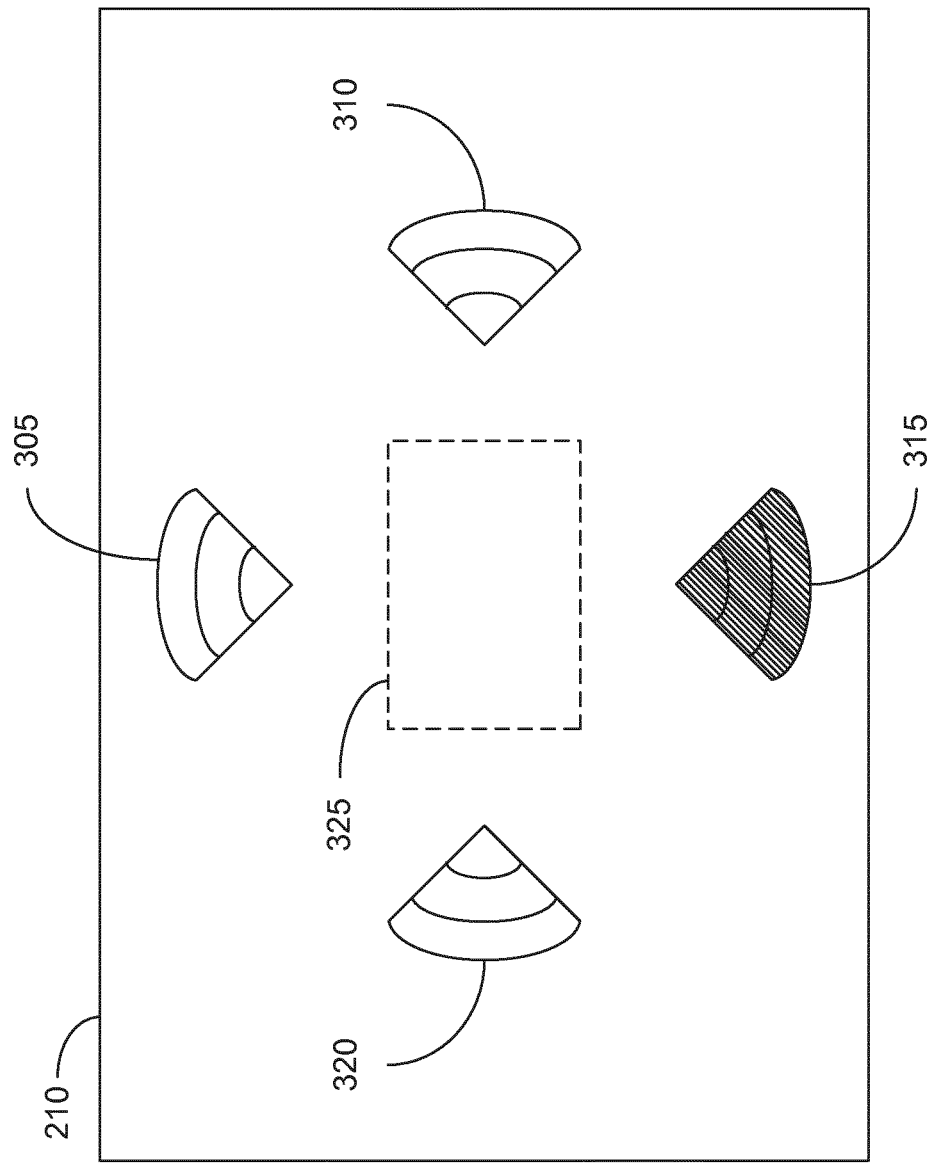
FIG. 3 depicts an exemplary view of a second portion of a digital display according to one or more aspects of the disclosed subjected matter.

FIG. 3 depicts an exemplary view of the second digital display 210 according to one or more aspects of the disclosed subjected matter. FIG. 3 can be a response screen displaying four response indicators 305, 310, 315, and 320, each positioned in a predetermined location in a spaced relationship. Additionally, the response indicators 305, 310, 315, and 320 can be various sizes. The position of each response indicator can be configured to reduce the likelihood that the test subject will accidentally swipe across more than one of the response indicators 305, 310, 315, and 320. A blank finger rest space 325 can be left open in a center area of the second digital display 210, on which the test subject can rest their finger while waiting to give a next response. Each response indicator 305, 310, 315, and 320 may be configured to receive more than just a quick tap to input an intended response. For example, each response indicator may include may include a plurality of response zones such that an input can be transmitted when all of the plurality of response zones in a response indicator have been selected. The response zones may be configured as a progression bar, for example, as shown in response indicator 315 which has been fully selected, which can result in the vision testing device 105 recording the "down" direction as the response for the vision test. A test subject may select all of the response zones of the response indicator by swiping continuously across all of the response zones. If a test subject selects only a subset of the response zones, a response is not recorded, giving the test subject an opportunity to select a different response indicator, thus reducing errors by the test subject. Results of the vision test can be recorded and transferred to a network, such as network 130, and/or another device, such as remote device 120. Alternatively, the response indicators can be displayed only on the first display screen and no response indicator is displayed on the second display screen. The user can select anywhere on the second display to begin the swipe as long as the swipe is in one of four directions corresponding to the response indicators and there is enough space between the start of the swipe and the edge of the second screen for the entire response indicator to be triggered.

Figure 4:
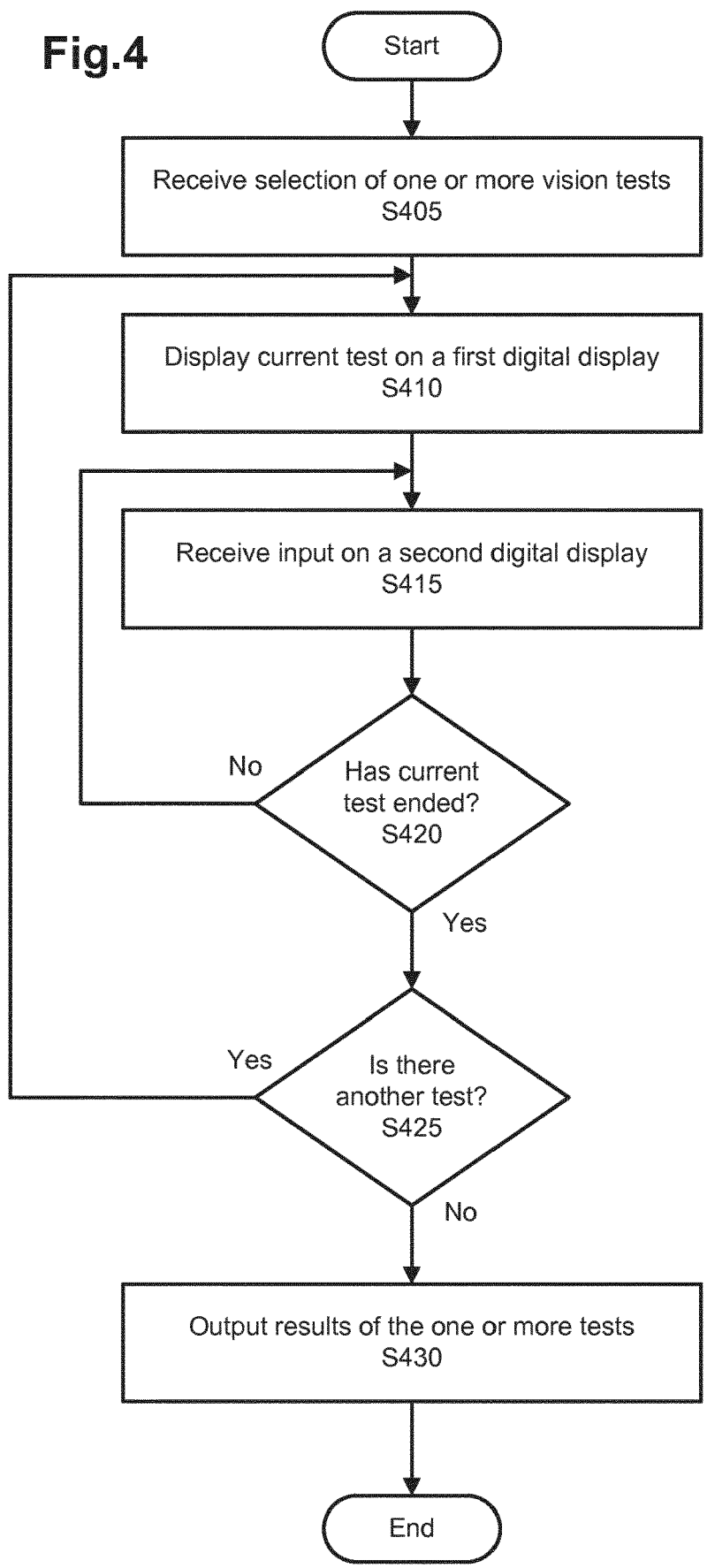
FIG. 4 is an algorithmic flow chart for administering one or more vision tests with the vision testing system according to one or more aspects of the disclosed subjected matter.

FIG. 4 is an algorithmic flow chart for administering one or more vision tests with the vision testing system 100 according to one or more aspects of the disclosed subjected matter.

In S405, selection of one or more vision tests can be received. For example, an operator can select one or more vision tests via the remote device 120. Alternatively, or additionally, one or more vision tests can have been previously selected for an auto-mode, which can subsequently be activated by the test subject. Additionally, a plurality of vision tests can be part of a protocol that can administer subsequent tests automatically.

In S410, a current test of the one or more selected tests can be displayed on the first portion of digital display 205. The test subject can view the current test on the first portion of the digital display 205 via the viewing station 215.

In S415, input, such as a touch-based swipe, for example, can be received on the second portion of the digital display 210. The received input can be a swipe as described in FIG. 3, for example. Alternatively, or additionally, the received input can be various other touch-based inputs corresponding to the current vision test being administered.

After input has been received via the second portion of the digital display 210, it can be determined if the current test has ended in S420. If the current test has not ended, the process can return to S415 to receive input via the second portion of the digital display 210. However, if the current test has ended, then it can be determined if there is another test in S425.

In S425, it can be determined if there is another vision test to be administered according to one or more exemplary aspects of the disclosed subject matter. For example, the operator may have selected a plurality of tests as part of a protocol designed for the test subject based on the needs of the test subject. For example, the needs of a military pilot may include a plurality of specific tests that may differ from a standard vision screening for a civilian patient/test subject trying to find out whether or not they need glasses. If it is determined that there is another test, the process can return to S410 to display the current test (e.g., next test in the protocol) on the first portion of the digital display 205. However, if there is not another test, such as an instance where there is only one test selected, it's the end of the protocol, and the like, then the results of the one or more vision tests can be output in S430. After the results of the one or more tests have been output, the process can end.

Figure 5:
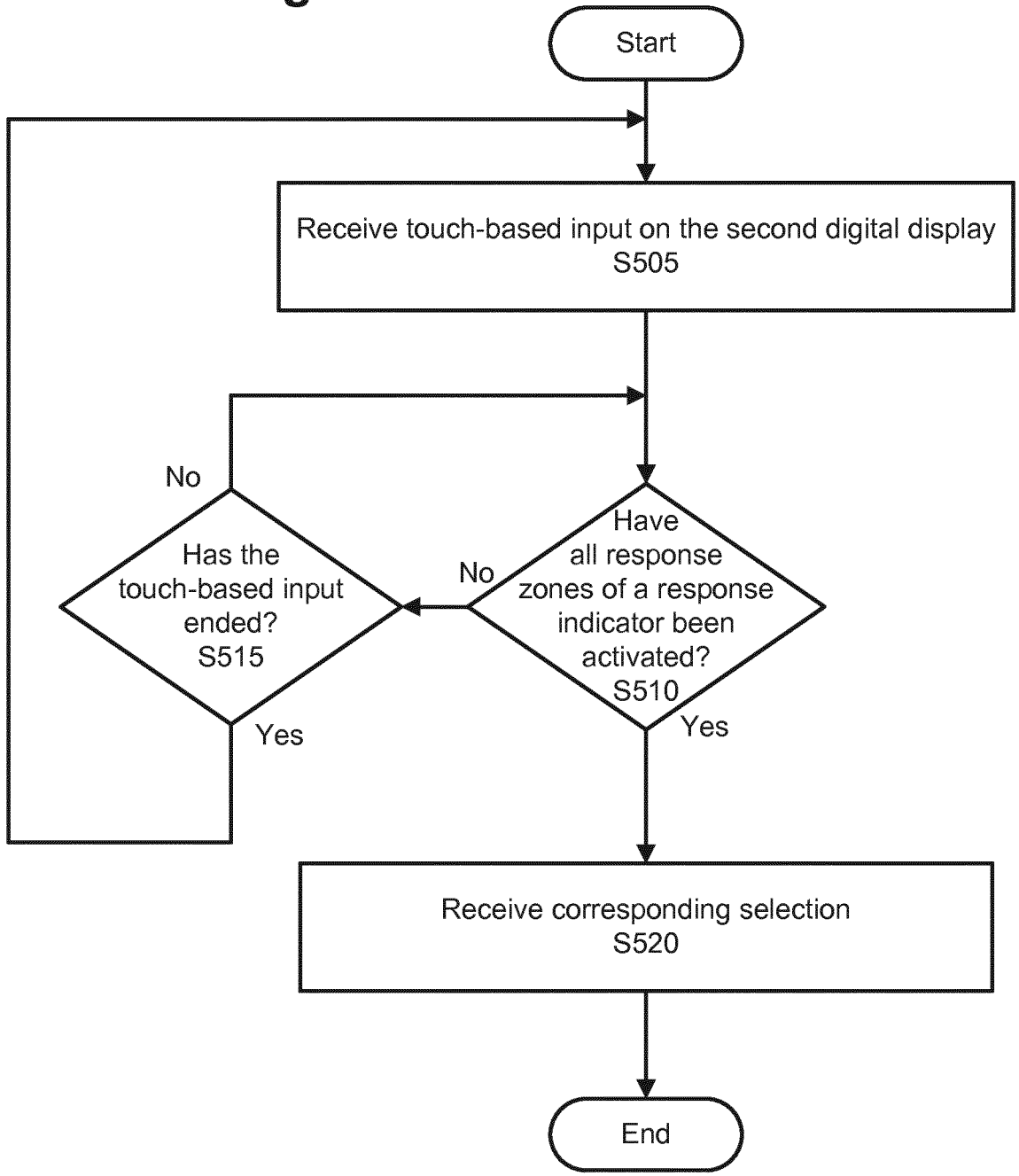
FIG. 5 is an algorithmic flow chart for receiving a selection via the second portion of the digital display according to one or more exemplary aspects of the disclosed subject matter.

FIG. 5 is an algorithmic flow chart for receiving a selection via the second portion of the digital display 210 according to one or more exemplary aspects of the disclosed subject matter.

In S505, touch-based input can be received on the second portion of the digital display 210. The touch-based input can be a swipe, for example.

In S510, it can be determined if all response zones of a response indicator, such as response indicator 305, 310, 315, 320, for example, have been activated. If it is determined that all response zones of the response indicator have been activated, such as response indicator 315, for example, then the corresponding selection, wherein the response indicator 315 can correspond to "down", for example, can be received in S520. However, if it is determined that not all response zones of the response indicator 305, 310, 315, 320 have been active, then it can be determined if the touch-based input has ended in S515.

In S515, it can be determined if the touch-based input, such as a swipe, for example, has ended. For example, it may be determined that the touch-based input has ended if the test subject stops touching the second portion of the digital display 210 or starts swiping in another direction. If it is determined that the touch-based input has not ended, then the process can return to S510 to determine if all response zones of a response indicator 305, 310, 315, 320 have been activated. However, if it is determined that the touch-based input has ended, the process can return to S505 to receive touch-based input on the second portion of the digital display 210.

In S520, the corresponding selection can be received. For example, each response indicator can correspond to a predetermined direction. When each response zone of a response indicator has been activated, the corresponding selection, or in other words, a selected direction, can be received. After the corresponding selection has been received, the process can end.

Figure 6:
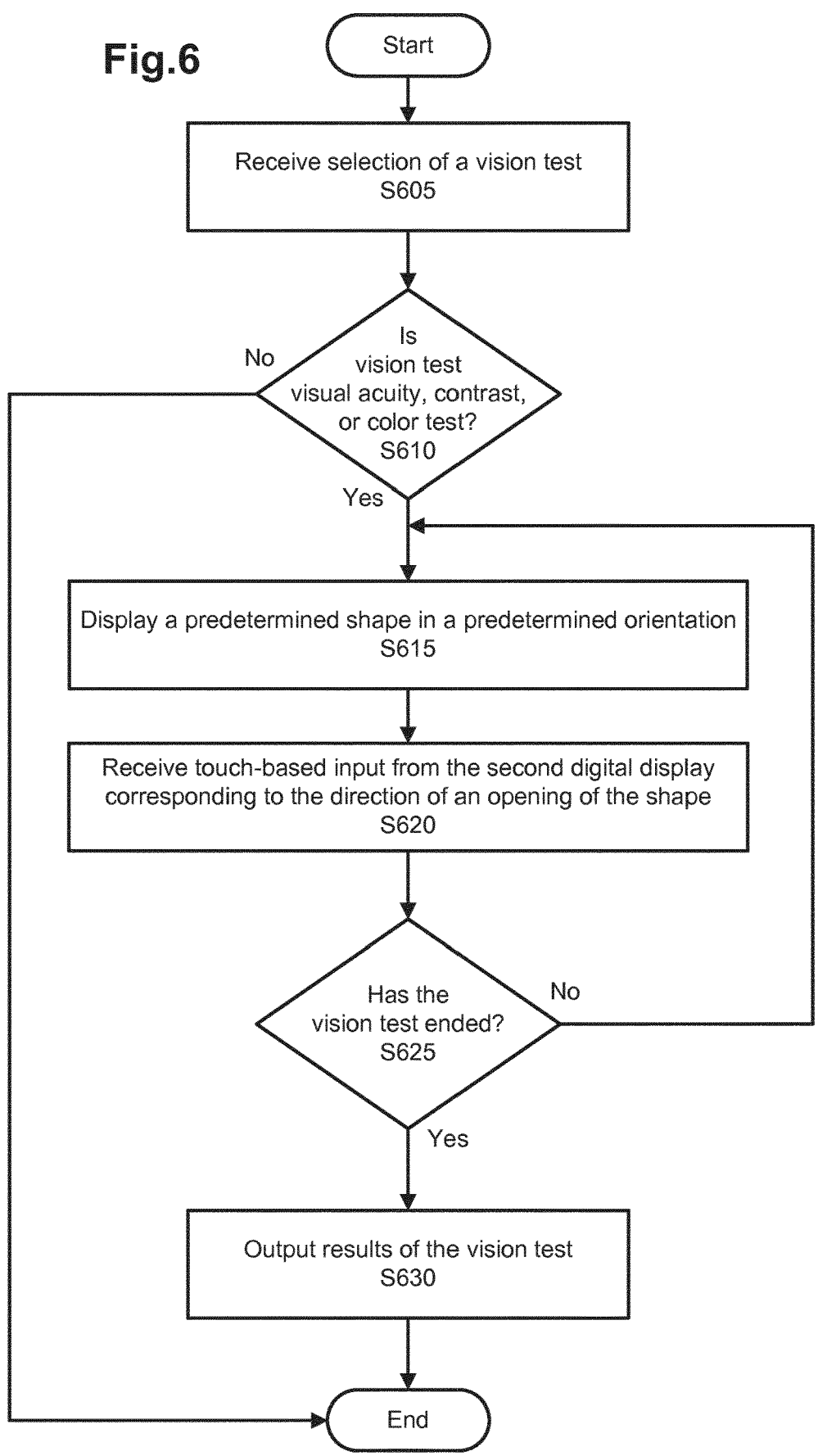
FIG. 6 is an algorithmic flow chart for administering a visual acuity, contrast, or color vision test according to one or more exemplary aspects of the disclosed subject matter.

FIG. 6 is an algorithmic flow chart for administering a visual acuity, contrast, or color vision test according to one or more exemplary aspects of the disclosed subject matter.

In S605, a vision test selection can be received. For example, the vision test can be selected via the remote device 120 and received by the vision testing device 105.

In S610, it can be determined if the selected vision test is a visual acuity vision test, a contrast vision test, or a color vision test. If the selected vision test is not one of a visual acuity vision test, a contrast vision test, or a color vision test, the process can end. However, if the selected vision test is one of a visual acuity vision test, a contrast vision test, or a color vision test, then a predetermined shape can be displayed in a predetermined orientation in S615.

In S615, the predetermined shape can be displayed in the predetermined orientation via the first portion of the digital display 105, for example. Additionally, the predetermined shape being displayed in the predetermined orientation can correspond to Landolts, for example. As further described herein, the Landolts, as well as other similar tests, can be administered for visual acuity, contrast, and color tests. For example, the visual acuity test can include the C-Landolt displayed in black with a white background. Alternatively, the C-Landolt can be displayed in white with a black background. It should be appreciated that the Tumbling E may also be used for the visual acuity test, for example. The contrast test may include the C-Landolt displayed in a gray level that can be adjustable so that the contrast between the C-Landolt and the background can change. A first color test can include the C-Landolt displayed in color. Additionally, the color of the C-Landolt can be configured to fade out because of a variation of contrast between the C-Landolt color displayed and its background. The second color test can include the Tumbling E in color.

In S620, touch-based input can be received from the second portion of the digital display 210, wherein the touch-based input can correspond to the direction of the opening of the shape. Alternatively, or additionally, the touch-based input can also correspond to the direction of the orientation of the shape. For example, even if the shape doesn't have an opening, the shape may be associated with predetermined orientations, such as an arrow, for example, such that the test subject may still swipe in a direction that corresponds to an orientation of the shape. The touch-based input indicating the direction of the opening can be a swipe movement as described in FIG. 3 and FIG. 5.

In S625, it can be determined if the selected vision test has ended. For example, it can be determined that the test has ended when the test subject gets two wrong answers on the same acuity level. Alternatively, the test can end if the test subject has completed the test without getting two wrong answers on the same level. For example, if the test has nine levels, the test subject may complete all nine levels without getting two wrong on the same level. If the selected vision test has not ended, the process can return to S615 to display a subsequent predetermined shape in a predetermined orientation. However, if the selected vision test has ended, the results of the vision test can be output in S630. After the results of the vision test have been output in S630, the process can end.

It should be appreciated that the process described in FIG. 6 is not limited to visual acuity, contrast, and color vision tests.

Figure 7:
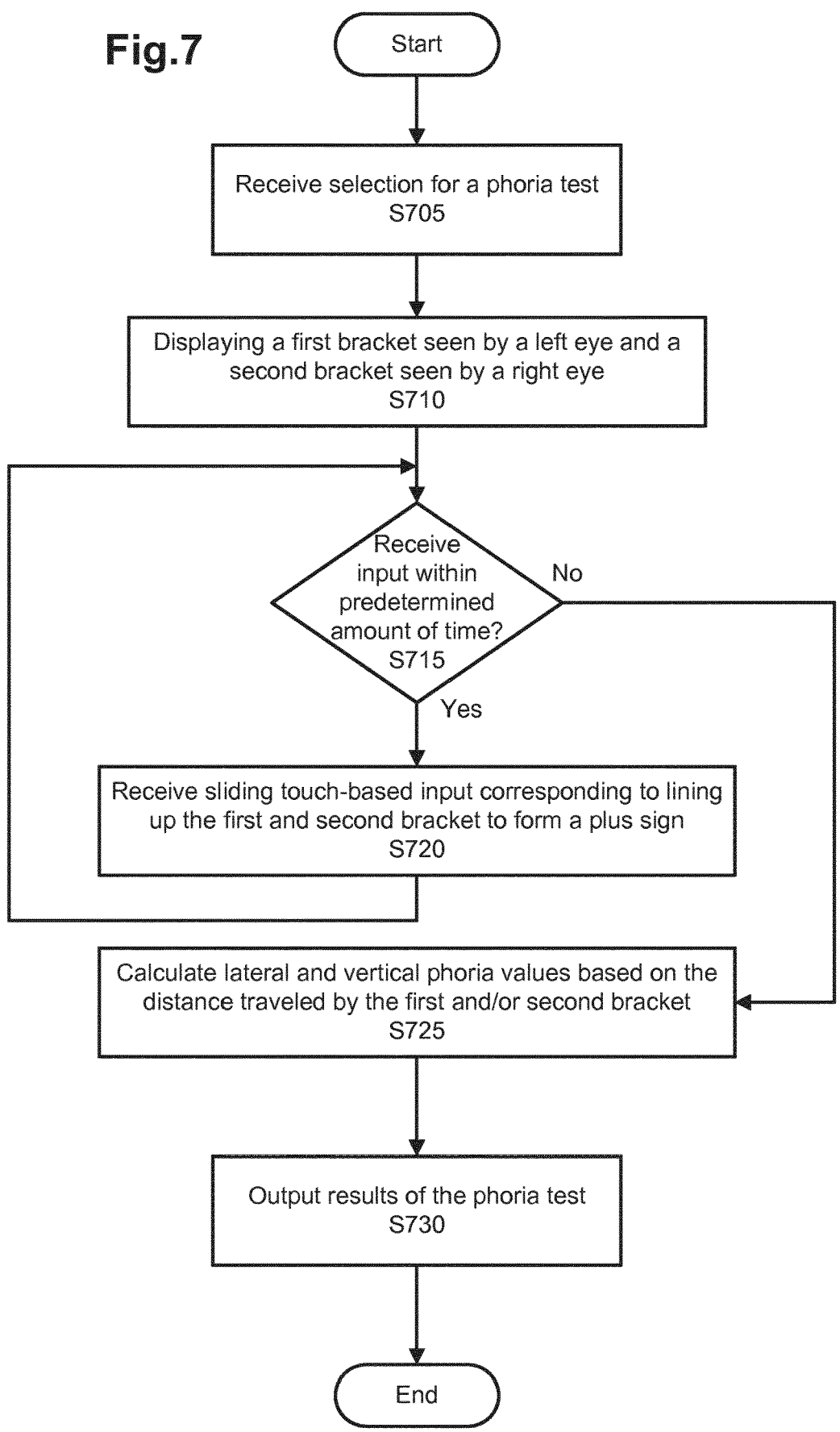
FIG. 7 is an algorithmic flow chart of administering a phoria test according to one or more exemplary aspects of the disclosed subject matter.

FIG. 7 is an algorithmic flow chart of administering a phoria test according to one or more exemplary aspects of the disclosed subject matter.

In S705, a selection for a phoria test can be received.

Figure 8A:
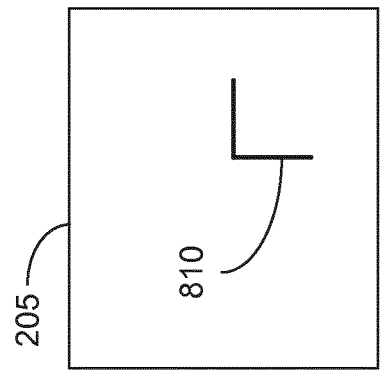
FIG. 8A depicts a first bracket seen by a left eye of the test subject according to one or more exemplary aspects of the disclosed subject matter.
Figure 8B:
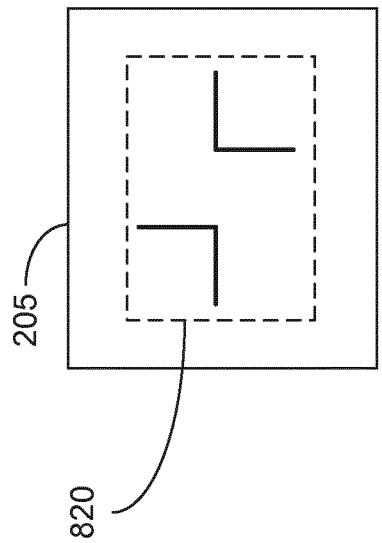
FIG. 8B depicts a second bracket seen by a right eye of the test subject according to one or more exemplary aspects of the disclosed subject matter.
Figure 8C:
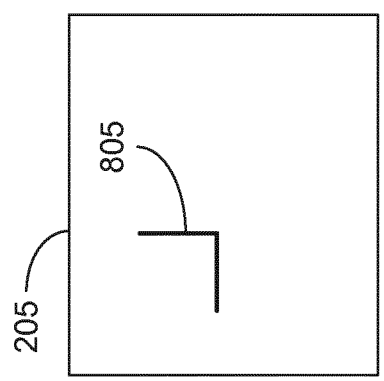
FIG. 8C depicts a plus sign displayed on the second portion of the digital display according to one or more exemplary aspects of the disclosed subject matter.

In S710, a first bracket seen by a left eye and a second bracket seen by a right eye can be displayed. For example, with reference to FIG. 8A and FIG. 8B, the first bracket 805 and the second bracket 810 can be displayed on the first portion of the digital display 205 such that the first bracket 805 can be seen by a left eye and the second bracket 810 can be seen by a right eye. The first bracket 805 can form a 90° angle starting at 90° and ending at 180°, and the second bracket 810 can form a 90° angle starting at 270° and ending at 360°. The goal can be to have the test subject see the brackets connected to form a plus sign 815 as displayed in FIG. 8C. However, if the test subject sees that the brackets 805, 810 are separated, as displayed as separated brackets 820 in FIG. 8D, the test subject may need to adjust the position of the brackets so the brackets can form the plus sign 815.

In S715, it can be determined if input, such as touch-based input via the second portion of the digital display 210, is received within a predetermined amount of time. The predetermined amount of time can be used to identify when the test subject has completed the phoria test. For example, after displaying the brackets, if there is no input received, the test can continue to calculate the lateral and vertical phoria values based on the distance traveled by the first and/or second brackets 805, 810 in S725. However, if the brackets did not move then the calculated values may be zero which can correspond to the test subject not having phoria. For example, when the brackets are displayed, the test subject may see the plus sign 815 as displayed in FIG. 8C, thereby not requiring any response from the test subject because the brackets already form the plus sign 815. Alternatively, if it is determined that input is received within the predetermined amount of time, sliding touch-based input can be received in S720.

In S720, sliding touch-based input can be received via the second portion of the digital display 210, wherein the sliding can correspond to lining up the first bracket 805 and the second bracket 810 in an attempt to form the plus sign 815. After receiving the sliding touch-based input, the process can return to S715 to determine if input is received within the predetermined amount of time, as the test subject may continue to adjust the positions of the brackets 805, 810. When it is determined that input has not been received within the predetermined amount of time, the lateral and vertical phoria values can be calculated in S720.

Figure 8D:
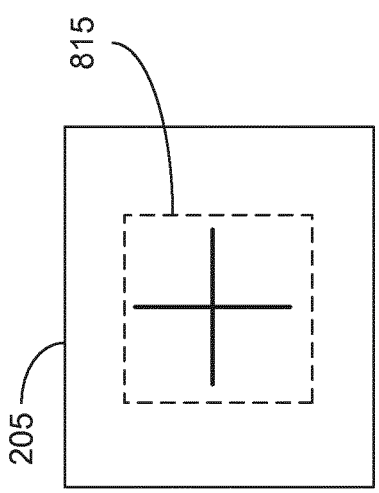
FIG. 8D depicts separated brackets displayed on the second portion of the digital display according to one or more exemplary aspects of the disclosed subject matter.

In S720, the lateral and vertical phoria values can be calculated based on the distance traveled by the first and/or second bracket 805, 810. For example, when the test subject first saw the brackets displayed, the brackets may have appeared as separated brackets 820 as shown in FIG. 8D. The test subject may have then attempted to move the brackets to form the plus sign 815. The phoria value calculation can be based on the distance that the separated brackets 820 moved to form the plus sign 815. The phoria value can have a precision of 0.1 diopter.

In S730, the results of the phoria test can be output. After the results of the phoria test are output, the process can end.

It should be appreciated that the process described in FIG. 7 is not limited to phoria tests.

FIG. 9A is a perspective view of a mask insert 905 component coupled to the vision testing device 205 according to one or more exemplary aspects of the disclosed subject matter. The LED strips 220a, 220b are depicted as described in FIG. 2. The mask insert 905 can be a visual field mask removably coupled to the viewing station 215 in a predetermined position. The mask insert 905 may be secured to the viewing station 215 via one or more of an adhesive strip and by setting the mask insert 905 in specific drill holes that may exist in the vision testing device 105, for example. The mask insert 905 can allow evaluation of a test subject's field of vision in all directions. The test subject's field of vision can be evaluated using a plurality of holes through which light from one or more LEDs can be visible. A portion of the plurality of holes in the mask insert 905 is highlighted by portion 910. The plurality of holes in the mask insert can be positioned in predetermined locations, each location corresponding to administering a field of vision test. For example, a test subject can receive the field of vision test by looking at a static point on the first digital display 205 and identifying when light from one or more LEDs is visible through one or more of the plurality of holes in the mask insert 905.

FIG. 9B is an exploded view of the mask insert 905 for the vision testing device 105 according to one or more exemplary aspects of the disclosed subject matter. The mask insert 905 can include a body 915, a transparent protective film 920, an assembly printed circuit card 925, a closure plate 930, and two magnet D5x3 NE53 binders 935. The one or more LEDs can be activated using the assembly printed circuit card 925. Additionally, the mask insert 905 is electronically coupled to the vision testing device 105 via the assembly printed circuit card 925 via a wire, for example, so that the assembly printed circuit card 925 may receive power for the one or more LEDs as well as communicate with the vision testing device 105. The transparent protective film 920 can be positioned between the assembly printed circuit card 925 and the body 915. The body 915 can include a plurality of holes, such as portion 910, for example, to assist in displaying the light from the LED in a predetermined way. For example, the body 905 may assist in the field of vision tests by allowing the light from the one or more LEDs to be seen in a predetermined way. For example, the body 915 may reduce the dispersion of the light so that a more accurate evaluation of field of vision may be determined. The closure plate 930 may assist in securing the transparent protective film 920 and the assembly printed circuit board 925 between the body 915 and the closure plate 930. Additionally, the two magnet binders 935 may assist in securing the mask insert 905 to the vision testing device 105. The field of vision test (perimetry test) may be administered in sections. More specifically, one or more LEDs may be activated to display light through one or more of the plurality of holes, and then wait a predetermined amount of time for the test subject's response. If the test subject answers, wherein the answer can be predetermined input on the second digital display 210, for example, within the predetermined amount of time, the vision testing system may record a correct response. However, if the test subject does not answer within the predetermined amount of time, the vision testing system 105 may record that the test subject did not see light displayed during that section of the field of vision test. After a section of the field of vision test has been completed, the next section of the test can be administered, and so on until the test has ended. The test may end after two incorrect responses, for example. Additionally, the locations at which the light is displayed through one or more of the plurality of holes in the mask insert 905 for a given section of the field of vision test may be randomized to prevent the test subject from attempting to anticipate where the light will be displayed for a subsequent section of the field of vision test.

Additionally, the times at which the LEDs are activated such that light can be seen through one or more of the plurality holes may be randomized to prevent false positives. For example, the test subject may not be able to see light through one of the plurality of holes, but still provide an input corresponding to having seen the light in that particular section of the test. By randomizing the timing at which the field of vision test progresses, false positives can be reduced. As a result, the test subject may need to provide an answer within a predetermined amount of time, by providing a predetermined input such as tapping on the second digital display 210, for example, before the vision testing device 105 determines that the test subject did not see light from the one or more predetermined holes at that section of the field of vision test.

Based on the predetermined positions of the plurality of holes in the mask inset 905, the mask insert 905 may be able to administer vertical peripheral vision tests as part of the field of vision tests. As a result, results for horizontal and vertical peripheral vision may be provided by the vision testing device 105 when using the mask insert 905. The mask insert 905 may also administer field of vision tests in conjunction with the LED pair 220a, 220b.

The mask insert 905 may also include a power cord that can be electrically coupled to a portion of the vision testing device 105 to provide power for the mask insert 905 which could power the one or more LEDs, for example.

FIG. 9C depicts light positions 940 in the mask insert 905 according to one or more aspects of the disclosed subject matter. The light positions 940 can be placed in several predetermined positions wherein the positions are optimized for administering a field of vision test. For example, for each of a right and a left eye piece, four light positions 940 can be at ten degrees radially from a center point, six light positions 940 can be placed at twenty degrees radially from the center point, and eight light positions 940 can be placed at thirty degrees radially from the center point. The center point can be a point at a center of each of a left eye piece and a right eye piece. The light positions 940 of 60 through 100 degrees can correspond to the positions of the lights in the LED pair 220a, 220b. Additionally, the light positions 940 corresponding to 45 degrees can be configured to be included with the vision testing device 105. The field of vision tests can be performed manually where the operator decides which light position 940 will be turned on. The light at the selected light positions 940 may be turned on briefly, such as for 300 milliseconds, for example. Alternatively, the field of vision test can be administered automatically wherein the lights in the light positions 940 may be turned on randomly, included no light being turned on at times. The test subject may be directed to provide input via the second portion of the digital display 210, for example, each time the test subject sees a light. The lights that have been seen by the test subject can be recorded, as well as how many the test subjected provided input when no light was turned on.

The system 100 includes several advantages regarding its wide range of applications, robustness, and significant time and cost savings. One example is the many advantages the system 100 can provide the military. For example, the system 100 can make use of the auto-mode to robustly test recruits as they enter basic training. This can save time and money by automating an eye exam portion of the general screening process via a protocol, for example, where a plurality of tests can be administered automatically while the system 100 can store scores associated with each test subject. Another example within the military could be vision tests for pilots. Pilots require excellent vision, and the status of their vision can be the difference in the pilot being able to continue flying or no longer being able to fly. This situation can put tremendous stress on an operator/optometrist. The system 100 provides robust and objective vision testing where an operator may be subject to pressure and/or bias.

Another advantage is that the system 100 can administer vision tests to recruits who may not be fluent in English because the system 100 can be configured to display visual instructions as well as refraining from proceeding with vision tests if the test subject does not understand the instructions. In traditional examinations, verbal/audio instructions could lead to errors in understanding which can generate more bias. These advantages are not limited to the military.

Further, the system 100 may provide many advantages to eye care professionals. Vision screening is used by eye care professionals to get a quick assessment of patient visual performance under various conditions including monocular which can focus on a left or right eye, binocular, night, day, far, near, intermediate, under glare, and the like. The purpose of the vision screening for the test subject may include sports/athletics, F.A.A. license, trouble reading, trouble seeing at night, and the like.

Ideally, the vision screening tests are as quick as possible, such as 1 to 2 minutes, for example, as the eye doctor will most likely conduct a thorough eye exam with refraction in addition to the screening tests. Therefore, the screening tests can serve as a starting point and/or to check specific conditions including glare, night/day, color, contrast, and the like.

The auto-mode can also include additional advantages. The auto-mode can be quick, accurate, non-operator dependent, non-voice dependent, and can be incorporated in the digital platform.

Typically, automatic modes use a simple "yes" button, which could correspond to clicking on a screen or a mechanical answer button, for example. The system has to ask, "If you see an 'A' press the button, if you see a 'B' press the button." There may be a 5 second delay before considering the answer is "no". This can lead to mistakes of understanding in letter recognition, such as P & B sounding the same, and a patient can give a false positive or negative.

Alternatively, the system 100 can provide an improved way to interact with the patient. Instead of a "yes" answer to a complex question, it displays standard C Landolt or E Landolt and asks in which direction it opens, for example. Test subjects can swipe on the digital display, wherein the digital display can be the second portion of the digital display 210, for example, in the direction of the opening, thereby reducing the misunderstanding on letters and providing four possible answers instead of a simple binary answer. Therefore, the system 100 can reduce wrong answers while saving time in performing the protocol.

Other advantages of the auto-mode include fully embedding the auto-mode in the system 100 so the auto-mode can benefit from all the functionality and features of the vision tests including light conditions, depth perception, distances, visual acuity, color, contrast, and the like. Additionally, it is robust and controlled which sets it apart from traditional charts.

More specifically, non-operator dependent can correspond to the test subject self-administer the vision test via the system 100, which can save time and improve the efficiency of the patient flow within an eye care practice, for example. The vison testing devices 105 can be installed in the pre-screening room and/or the dispensing area, saving valuable time for the doctor in the exam lane, for example. It can also remove subjectivity and/or bias from the operator, thereby allowing for a more objective result.

More specifically regarding the non-audio dependent advantages, preliminary instructions may be given in three different ways including voice, text, and pictograms as a trial test. Therefore the patient is guided in how to perform the test and there is always an instruction that the test subject can understand, regardless of language, hearing, and/or reading capacities. The vision test process does not start until the trial test is answered correctly to ensure understanding. Once the vision test starts, the test can be administered automatically without further instructions. The non-audio dependent testing may be advantageous for deaf patients.

Another advantage of the system 100 is that the test protocols used in the auto-mode can be configured by building a protocol with a plurality of tests. Once a test protocol is launched, it can progress independently and automatically, recording the test subject's answers. For example, in the C-Landolt acuity test, each time the test subject answers correctly by swiping in the right direction, the next C-Landolt is automatically displayed with a smaller acuity. When answered incorrectly, the vision testing device 105 goes back to the previous acuity level. If answered twice incorrectly for the same level, the process stops and move to the next test.

The follow advantages can be considered even further. The vision testing system 100 is non-operator dependent. Therefore, the system 100 is more objective by removing subjective interaction with an operator. It also saves time so the operator can perform other tasks, thereby increasing productivity and reducing operating costs.

Because the system 100 can be non-voice dependent, any bias linked with audio recognition, such as "P" and "B" sounding similar, for example, may be removed, thereby causing fewer errors and providing more accuracy.

The speed at which the vision tests can be administered can be significantly increased based on automatic slide progression, instant recording of answers, fewer questions needed, and the like.

Additionally, benefits from all the features and functions of the vision testing devices 105 include a plurality of types of test and types of conditions.

Further, significant customization is available. For example, pre-programmed protocols, wherein protocols can be a plurality of tests administered in succession, including the various conditions options can fit practice and patient needs.

The system 100 is also robust. For example, the totality of the second digital display 210 can be used to "swipe". More specifically, it is the direction of the swipe that is considered rather than clicking on a screen area of buttons. The swipe movement can be long enough to fill up 3 progression bars, wherein the 3 progression bars can correspond to response zones in the response indicator 305, 310, 315, 320, for example, which can avoid errors associated with just "clicking". Only when the response indicator is full, such as the response indicator 315, for example, the answer is validated and confirmed. If the test subject has second thoughts, the test subject can stop the movement before completing the swipe in another direction.

Next, a hardware description of the remote device 120 according to exemplary embodiments is described with reference to FIG. 10. It should be appreciated that the hardware description may apply to the server 125 and the vision testing device 105. In FIG. 10, the remote device 120 includes a CPU 1000 which performs the processes described above/below. The process data and instructions may be stored in memory 1002. These processes and instructions may also be stored on a storage medium disk 1004 such as a hard drive or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the remote device 120 communicates, such as a server or computer.

Further, the claimed advancements may be provided as a utility application, background daemon, or component of an operating system, or combination thereof, executing in conjunction with CPU 1000 and an operating system such as Microsoft Windows 7, UNIX, Solaris, LINUX, Apple MAC-OS and other systems known to those skilled in the art.

The hardware elements in order to achieve the remote device 120 may be realized by various circuitry elements, known to those skilled in the art. For example, CPU 1000 may be a Xenon or Core processor from Intel of America or an Opteron processor from AMD of America, or may be other processor types that would be recognized by one of ordinary skill in the art. Alternatively, the CPU 1000 may be implemented on an FPGA, ASIC, PLD or using discrete logic circuits, as one of ordinary skill in the art would recognize. Further, CPU 1000 may be implemented as multiple processors cooperatively working in parallel to perform the instructions of the inventive processes described above.

The remote device 120 in FIG. 10 also includes a network controller 1006, such as an Intel Ethernet PRO network interface card from Intel Corporation of America, for interfacing with network 130. As can be appreciated, the network 130 can be a public network, such as the Internet, or a private network such as an LAN or WAN network, or any combination thereof and can also include PSTN or ISDN subnetworks. The network 130 can also be wired, such as an Ethernet network, or can be wireless such as a cellular network including EDGE, 3G and 4G wireless cellular systems. The wireless network can also be WiFi, Bluetooth, or any other wireless form of communication that is known.

The remote device 120 further includes a display controller 1008, such as a NVIDIA GeForce GTX or Quadro graphics adaptor from NVIDIA Corporation of America for interfacing with display 1010, such as a Hewlett Packard HPL2445w LCD monitor. A general purpose I/O interface 1012 interfaces with a keyboard and/or mouse 1014 as well as a touch screen panel 1016 on or separate from display 1010. General purpose I/O interface also connects to a variety of peripherals 1018 including printers and scanners, such as an OfficeJet or DeskJet from Hewlett Packard.

A sound controller 1020 is also provided in the remote device 120, such as Sound Blaster X-Fi Titanium from Creative, to interface with speakers/microphone 1022 thereby providing sounds and/or music.

The general purpose storage controller 1024 connects the storage medium disk 1004 with communication bus 1026, which may be an ISA, EISA, VESA, PCI, or similar, for interconnecting all of the components of the remote device 120. A description of the general features and functionality of the display 1010, keyboard and/or mouse 1014, as well as the display controller 1008, storage controller 1024, network controller 1006, sound controller 1020, and general purpose I/O interface 1012 is omitted herein for brevity as these features are known.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

The functions and features described herein may also be executed by various distributed components of a system. For example, one or more processors may execute these system functions, wherein the processors are distributed across multiple components communicating in a network. The distributed components may include one or more client and server machines, which may share processing, in addition to various human interface and communication devices including display monitors, smart phones, tablets, personal digital assistants, and the like. The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

(1) A vision testing system, comprising a vision testing apparatus including a light-occluding casing, a viewing station coupled to the light-occluding casing, a first digital display housed within the light-occluding casing, a second digital display external to the light-occluding casing that is configured to receive touch-based input, and processing circuitry configured to display one or more predetermined vision tests via the first digital display, receive input via the second digital display, the second digital display having a plurality of response indicators, each response indicator having a plurality of response zones, wherein the second digital display records a response upon selection of each of the response zones of a respective response indicator, and determine results for the one or more predetermined vision tests based on the input received via the second digital display;

(2) The vision testing system of claim (1), wherein the processing circuitry is further configured to transmit the results of the one or more vision tests to a remote device communicably coupled to the vision testing apparatus.

(3) The vision testing system of claim (1)-(2), wherein the second digital display is configured to detect a swipe input, the swipe input being based on direction and length, wherein the length of the swipe is sufficient to select each of the response zones of the respective response indicator.

(4) The vision testing system of claim (1)-(3), wherein the processing circuitry is further configured to administer one or more vision tests, wherein administering one or more of the vision tests includes displaying one or more predetermined shapes in a predetermined orientation a predetermined number of times, receiving input from the second digital display corresponding to a direction of an orientation of the one or more predetermined shapes for each time the one or more predetermined shapes in the predetermined orientation is displayed, transmitting a result of one or more of the vision tests to the remote device.

(5) The vision testing system of claim (1)-(4), wherein the indication of the direction of the orientation of the one or more predetermined shapes via the second digital display includes one or more of a touch on a predetermined location of the second digital display corresponding to the orientation and a swipe from a first location on the second digital display toward a second location on the second digital display.

(6) The vision testing system of claim (1)-(5), wherein the processing circuitry is further configured to administer a phoria test, wherein administering the phoria test includes displaying a first bracket seen by a left eye, the first bracket forming a 90° angle starting at 90° and ending at 180°, and a second bracket seen by a right eye, the second bracket forming a 90° angle starting at 270° and ending at 360°, when receiving no input via the second digital display after a predetermined amount of time when the first bracket and the second bracket align to form a predetermined shape, transmitting a result to the remote device, the result corresponding to the phoria test indicating that no phoria is detected, and when receiving input via the second digital display corresponding to sliding a finger in one or more directions on the second digital display, wherein sliding the finger in one or more directions corresponds to an attempt to line up the first bracket and the second bracket to form the predetermined shape, transmitting lateral and vertical phoria values to the remote device, the lateral and vertical phoria values being based on the distance the first and second bracket traveled to form the predetermined shape;

(7) The vision testing system of claim (1)-(6), wherein the lateral and vertical phoria values have a precision of 0.1 diopter.

(8) A method of administering vision tests, comprising: displaying one or more predetermined vision tests via a first digital display, the first digital display being housed in a light-occluding casing; receiving input via a second digital display, the second digital display being external to the light-occluding casing, the second digital display having a plurality of response indicators, each response indicator having a plurality of response zones, wherein the second digital display records a response upon selection of each of the response zones of a respective response indicator; and determining, via processing circuitry, results for the one or more predetermined vision tests based on the input received via the second digital display.

(9) The method of claim (8), further comprising: transmitting the results of the one or more vision tests to a remote device communicably coupled to a vision testing apparatus, the vision testing apparatus including the first digital display and the second digital display.

(10) The method of claim (8)-(9), wherein the one or more predetermined vision tests include preliminary tests, refractive tests, non-refractive tests, a horizontal peripheral vision test, HOTV tests, road sign recognition, and Allen tests.

(11) The method of claim (8)-(10), wherein the second digital display further comprises: detecting a swipe input, the swipe input being based on direction and length, wherein the length of the swipe is sufficient to select each of the response zones of the respective response indicator.

(12) The method of claim (8)-(11), further comprising administering one or more vision tests, wherein administering one or more of the vision tests includes displaying one or more predetermined shapes in a predetermined orientation a predetermined number of times, receiving input from the second digital display corresponding to a direction of an orientation of the one or more predetermined shapes for each time the one or more predetermined shapes in the predetermined orientation is displayed, transmitting a result of one or more of the vision tests to the remote device.

(13) The method of claim (8)-(12), wherein the indication of the direction of the orientation of the one or more predetermined shapes via the second digital display includes one or more of a touch on a predetermined location of the second digital display corresponding to the orientation and a swipe from a first location on the second digital display toward a second location on the second digital display.

(14) The method of claim (8)-(13), further comprising administering a phoria test, wherein administering the phoria test includes displaying, on the first digital display, a first bracket seen by a left eye, the first bracket forming a 90° angle starting at 90° and ending at 180°, and a second bracket seen by a right eye, the second bracket forming a 90° angle starting at 270° and ending at 360°, when receiving no input via the second digital display after a predetermined amount of time when the first bracket and the second bracket align to form a predetermined shape, transmitting a result to the remote device, the result corresponding to the phoria test indicating that no phoria is detected, and when receiving input via the second digital display corresponding to sliding a finger in one or more directions on the second digital display, wherein sliding the finger in one or more directions corresponds to an attempt to line up the first bracket and the second bracket to form the predetermined shape, transmitting lateral and vertical phoria values to the remote device, the lateral and vertical phoria values being based on the distance the first and second bracket traveled to form the predetermined shape.

(15) The method of claim (8)-(14), wherein the lateral and vertical phoria values have a precision of 0.1 diopter.

(16) The vision testing system of claim (1)-(7) wherein the second digital display records a response only upon selection of each of the response zones of a respective response indicator.

(17) The method of claim (8)-(15), further comprising: recording a response only upon selection of each of the response zones of a respective response indicator.

(18a) The vision testing system of claim (1)-(7), wherein the one or more predetermined vision tests include preliminary tests, refractive tests, non-refractive tests, a horizontal peripheral vision test, HOTV tests, road sign recognition, and Allen tests.

(18b) The vision testing system of claim (16), wherein the one or more predetermined vision tests include preliminary tests, refractive tests, non-refractive tests, a horizontal peripheral vision test, HOTV tests, road sign recognition, and Allen tests.

(19) A non-transitory computer-readable storage medium storing computer readable instructions that, when executed by a computer, cause the computer to perform the method, comprising: displaying one or more predetermined vision tests via a first digital display, the first digital display being housed in a light-occluding casing; receiving input via a second digital display, the second digital display being external to the light-occluding casing, the second digital display having a plurality of response indicators, each response indicator having a plurality of response zones, wherein the second digital display records a response upon selection of each of the response zones of a respective response indicator; and determining results for the one or more predetermined vision tests based on the input received via the second digital display.

(20) The non-transitory computer-readable storage medium of (19), further comprising administering a phoria test, wherein administering the phoria test includes displaying, on the first digital display, a first bracket seen by a left eye, the first bracket forming a 90° angle starting at 90° and ending at 180°, and a second bracket seen by a right eye, the second bracket forming a 90° angle starting at 270° and ending at 360°, when receiving no input via the second digital display after a predetermined amount of time when the first bracket and the second bracket align to form a predetermined shape, transmitting a result to the remote device, the result corresponding to the phoria test indicating that no phoria is detected, and when receiving input via the second digital display corresponding to sliding a finger in one or more directions on the second digital display, wherein sliding the finger in one or more directions corresponds to an attempt to line up the first bracket and the second bracket to form the predetermined shape, transmitting lateral and vertical phoria values to the remote device, the lateral and vertical phoria values being based on the distance the first and second bracket traveled to form the predetermined shape.

(21) The non-transitory computer-readable storage medium of (19)-(20), wherein the lateral and vertical phoria values have a precision of 0.1 diopter.

(22) The non-transitory computer-readable storage medium of (19)-(21), further comprising administering one or more vision tests, wherein administering one or more of the vision tests includes displaying one or more predetermined shapes in a predetermined orientation a predetermined number of times, receiving input from the second digital display corresponding to a direction of an orientation of the one or more predetermined shapes for each time the one or more predetermined shapes in the predetermined orientation is displayed, transmitting a result of one or more of the vision tests to the remote device.

(23) The non-transitory computer-readable storage medium of (19)-(22), wherein the indication of the direction of the orientation of the one or more predetermined shapes via the second digital display includes one or more of a touch on a predetermined location of the second digital display corresponding to the orientation and a swipe from a first location on the second digital display toward a second location on the second digital display.

(24) The vision testing system of (1)-(7), (16), and (18), wherein the plurality of response zones in each response indicator are aligned in a cardinal direction.

(25) The method of (8)-(15) and (17), wherein the plurality of response zones in each response indicator are aligned in a cardinal direction.

(26) The non-transitory computer-readable medium of (19)-(23), wherein the plurality of response zones in each response indicator are aligned in a cardinal direction.

(27) The vision testing system of (1)-(7), (16), (18), and (24), wherein content displayed via the first digital display changes in response to input from the second digital display.

(28) The method of (8)-(15), (17), and (25), wherein content displayed via the first digital display changes in response to input from the second digital display.

(29) The non-transitory computer-readable medium of (19)-(23) and (26), wherein content displayed via the first digital display changes in response to input from the second digital display.

(30) The vision testing system of (1)-(7), (16), (18), (24), and (27), wherein the first digital display and the second digital display are predetermined portions of one digital display.

(31) The method of (8)-(15), (17), (25), and (28) wherein the first digital display and the second digital display are predetermined portions of one digital display.

(32) The non-transitory computer-readable medium of (19)-(23) (26), and (29), wherein the first digital display and the second digital display are predetermined portions of one digital display.

(33) The vision testing system of (1)-(7), (16), (18), (24), (27), and (30), wherein the second digital display is a touchpad.

(34) The vision testing system of (1)-(7), (16), (18), (24), (27), (30), and (33), wherein the vision testing apparatus includes a mask insert removably coupled to the viewing station, the removable mask insert being configured for a vertical peripheral vision test.

(35) The method of (8)-(15), (17), (25), (28), and (31), wherein the one or more vision tests include a vertical peripheral vision test, wherein the vertical peripheral vision test includes a removable mask insert.

(36) The non-transitory computer-readable medium of (19)-(23) (26), (29), and (32), wherein the one or more vision tests include a vertical peripheral vision test, wherein the vertical peripheral vision test includes a removable mask insert.

(37) The vision testing system of (1)-(7), (16), (18), (24), (27), (30), (33), and (34) wherein the one or more vision tests include a visual acuity test, a color test, and a contrast test.

(38) The method of (8)-(15), (17), (25), (28), and (35), wherein the one or more vision tests include a visual acuity test, a color test, and a contrast test.

(39) The non-transitory computer-readable medium of (19)-(23) (26), (29), (32), and (36), wherein the one or more vision tests include a visual acuity test, a color test, and a contrast test.

Having now described embodiments of the disclosed subject matter, it should be apparent to those skilled in the art that the foregoing is merely illustrative and not limiting, having been presented by way of example only. Thus, although particular configurations have been discussed herein, other configurations can also be employed. Numerous modifications and other embodiments, such as combinations, rearrangements, and the like, for example, are enabled by the present disclosure and are within the scope of one of ordinary skill in the art and are contemplated as falling within the scope of the disclosed subject matter and any equivalents thereto. Features of the disclosed embodiments can be combined, rearranged, omitted, etc., within the scope of the invention to produce additional embodiments. Furthermore, certain features may sometimes be used to advantage without a corresponding use of other features. Accordingly, Applicant(s) intend(s) to embrace all such alternatives, modifications, equivalents, and variations that are within the spirit and scope of the disclosed subject matter.

The invention claimed is:
1. A vision testing system, comprising:
a vision testing apparatus including
a light-occluding casing,
a viewing station coupled to the light-occluding casing,
a first digital display housed within the light-occluding casing,
a second digital display external to the light-occluding casing that is configured to receive touch-based input, and
processing circuitry configured to
display one or more predetermined vision tests via the first digital display,
receive input via the second digital display, the second digital display having a plurality of response indicators, each response indicator having a plurality of response zones, and
determine results for the one or more predetermined vision tests based on the input received via the second digital display,
wherein the second digital display is configured to detect a swipe input, the swipe input being based on direction and length, and wherein the second digital display is configured to record a response when the length of the swipe is sufficient to select all of the plurality of the response zones of the respective response indicator, the response not being recorded when a subset of the plurality of the response zones is selected, and
wherein the processing circuitry is further configured to administer a phoria test, wherein administering the phoria test includes:
displaying a first bracket seen by a left eye, the first bracket forming a 90° angle starting at 90° and ending at 180°, and a second bracket seen by a right eye, the second bracket forming a 90° angle starting at 270° and ending at 360°, when receiving no input via the second digital display after a predetermined amount of time when the first bracket and the second bracket align to form a predetermined shape, transmitting a result to the remote device, the result corresponding to the phoria test indicating that no phoria is detected, and when receiving input via the second digital display corresponding to sliding a finger in one or more directions on the second digital display, wherein sliding the finger in one or more directions corresponds to an attempt to line up the first bracket and the second bracket to form the predetermined shape, transmitting lateral and vertical phoria values to the remote device, the lateral and vertical phoria values being based on the distance the first and second bracket traveled to form the predetermined shape.

2. The vision testing system of claim 1, wherein the processing circuitry is further configured to
transmit the results of the one or more vision tests to a remote device communicably coupled to the vision testing apparatus.

3. The vision testing system of claim 1, wherein the processing circuitry is further configured to administer one or more vision tests, wherein administering one or more of the vision tests includes
displaying one or more predetermined shapes in a predetermined orientation a predetermined number of times,
receiving input from the second digital display corresponding to a direction of an orientation of the one or more predetermined shapes for each time the one or more predetermined shapes in the predetermined orientation is displayed,
transmitting a result of one or more of the vision tests to a remote device.

4. The vision testing system of claim 3, wherein the indication of the direction of the orientation of the one or more predetermined shapes via the second digital display includes one or more of a touch on a predetermined location of the second digital display corresponding to the orientation and a swipe from a first location on the second digital display toward a second location on the second digital display.

5. The vision testing system of claim 1, wherein the lateral and vertical phoria values have a precision of 0.1 diopter.

6. A method of administering vision tests, comprising:
displaying one or more predetermined vision tests via a first digital display, the first digital display being housed in a light-occluding casing;
receiving input via a second digital display, the second digital display being external to the light-occluding casing, the second digital display having a plurality of response indicators, each response indicator having a plurality of response zones;
determining, via processing circuitry, results for the one or more predetermined vision tests based on the input received via the second digital display,
wherein receiving input via the second digital display comprises:
detecting a swipe input, the swipe input being based on direction and length, wherein the second digital display records a response when the length of the swipe is sufficient to select all of the plurality of the response zones of the respective response indicator, the response not being recorded when a subset of the plurality of the response zones is selected; and
administering a phoria test, wherein administering the phoria test includes:

displaying, on the first digital display, a first bracket seen by a left eye, the first bracket forming a 90° angle starting at 90° and ending at 180°, and a second bracket seen by a right eye, the second bracket forming a 90° angle starting at 270° and ending at 360°, when receiving no input via the second digital display after a predetermined amount of time when the first bracket and the second bracket align to form a predetermined shape, transmitting a result to the remote device, the result corresponding to the phoria test indicating that no phoria is detected, and when receiving input via the second digital display corresponding to sliding a finger in one or more directions on the second digital display, wherein sliding the finger in one or more directions corresponds to an attempt to line up the first bracket and the second bracket to form the predetermined shape, transmitting lateral and vertical phoria values to the remote device, the lateral and vertical phoria values being based on the distance the first and second bracket traveled to form the predetermined shape.

7. The method of claim 6, further comprising:
transmitting the results of the one or more vision tests to a remote device communicably coupled to a vision testing apparatus, the vision testing apparatus including the first digital display and the second digital display.

8. The method of claim 6, wherein the one or more predetermined vision tests include preliminary tests, refractive tests, non-refractive tests, a horizontal peripheral vision test, HOTV tests, road sign recognition, and Allen tests.

9. The method of claim 6, further comprising administering one or more of a vision test, wherein administering one or more of the vision tests includes
displaying one or more predetermined shapes in a predetermined orientation a predetermined number of times,
receiving input from the second digital display corresponding to a direction of an orientation of the one or more predetermined shapes for each time the one or more predetermined shapes in the predetermined orientation is displayed,
transmitting a result of one or more of the vision tests to the remote device.

10. The method of claim 9, wherein the indication of the direction of the orientation of the one or more predetermined shapes via the second digital display includes one or more of a touch on a predetermined location of the second digital display corresponding to the orientation and a swipe from a first location on the second digital display toward a second location on the second digital display.

11. The method of claim 6, wherein the lateral and vertical phoria values have a precision of 0.1 diopter.

12. A vision testing system, comprising:
a vision testing apparatus including
a light-occluding casing,
a viewing station coupled to the light-occluding casing,
a first digital display housed within the light-occluding casing,
a second digital display external to the light-occluding casing that is configured to receive touch-based input, and
processing circuitry configured to
display one or more predetermined vision tests via the first digital display,
receive input via the second digital display, the second digital display having a plurality of response indicators, each response indicator having a plurality of response zones, wherein the second digital display records a response upon selection of each of the response zones of a respective response indicator, and determine results for the one or more predetermined vision tests based on the input received via the second digital display, wherein the processing circuitry is further configured to administer a phoria test, wherein administering the phoria test includes displaying a first bracket seen by a left eye, the first bracket forming a 90° angle starting at 90° and ending at 180°, and a second bracket seen by a right eye, the second bracket forming a 90° angle starting at 270° and ending at 360°, when receiving no input via the second digital display after a predetermined amount of time when the first bracket and the second bracket align to form a predetermined shape, transmitting a result to the remote device, the result corresponding to the phoria test indicating that no phoria is detected, and when receiving input via the second digital display corresponding to sliding a finger in one or more directions on the second digital display, wherein sliding the finger in one or more directions corresponds to an attempt to line up the first bracket and the second bracket to form the predetermined shape, transmitting lateral and vertical phoria values to the remote device, the lateral and vertical phoria values being based on the distance the first and second bracket traveled to form the predetermined shape.

* * * * *